United States Patent [19]

De Simone

[11] 4,198,395

[45] Apr. 15, 1980

[54] NOVEL HYPOCHOLESTEROLEMIC RESIN

[75] Inventor: Renato De Simone, Salerno, Italy

[73] Assignee: Etablissement Viridis, Vaduz, Liechtenstein

[21] Appl. No.: 800,526

[22] Filed: May 25, 1977

[30] Foreign Application Priority Data

May 25, 1976 [FR] France ................................ 76 15734

[51] Int. Cl.$^2$ ....................... A61K 31/785; C08J 9/20; C08J 9/36
[52] U.S. Cl. .............................. 424/79; 260/DIG. 47; 521/32; 526/199; 526/336
[58] Field of Search .................... 260/2.1 E, DIG. 47; 424/79; 521/32

[56] References Cited

U.S. PATENT DOCUMENTS 3,637,535  1/1972  Corte et al. ........................... 260/2.1

FOREIGN PATENT DOCUMENTS 849122   9/1960  United Kingdom ................. 260/2.1 E
929391   6/1963  United Kingdom ............ 260/DIG. 47
1286949  8/1972  United Kingdom ............ 260/DIG. 47

*Primary Examiner*—Stanford M. Levin
*Attorney, Agent, or Firm*—Joseph W. Molasky & Associates

[57] ABSTRACT

A novel microporous resin which is useful in the treatment of hyperchloesterolemia. This resin is comprised of a cross-linked polystyrene matrix and is characterized by active moieties selected from among methylamino, methylammonium or a combination of methylamino and methylammonium groups. The porosity of this resin is capable of absorbing and retaining bile salts having an average diameter of 150–200 Angstrom units.

10 Claims, No Drawings

NOVEL HYPOCHOLESTEROLEMIC RESIN

This invention relates to a new microporous ion exchange resin for use in human therapy as a hypocholesterolemic agent. Ion exchange resins notably find use in the treatment of various pathological states such as hyperacidity, prevention of $Na^+$ depletion in the gastroenteric tract, induction of $K^+$ depletion, nephrotic, pancreatic and cardiac treatment, ulcer treatment, neutralization of gastric acidity etc.

Obviously each particular pathological state requires a resin of particular chemical characteristics, chosen from the group consisting of weakly acid resins, strongly acid resins, weakly basic resins, and strongly basic resins, a fundamental requirement being that the resins are free from toxicity towards the human organism.

The use of ion exchange resins has notably been extended in recent years to the treatment of hyperlipidemia.

In this respect, with excessive levels of lipids, which are essentially cholesterol, premature arteriosclerosis can develop in the organism with consequences such as cardiac infarction and cerebral thrombosis. It is therefore a problem of large dimensions for which the resolutive drug has not yet been found.

To reduce the cholesterol to normal levels, it is necessary to act in two directions, by excluding all foods rich in cholesterol or saturated fats, and by increasing the elimination of the cholesterol. Basic ion exchange resins act in this second manner by fixing the bile acids at the intestinal level, and thus interrupting their enterohepatic recycle with consequent loss of cholesterol. The basic ammonium and amino resins used up to the present time (essentially Cholestiramine—B.P. No. 929,391) have a maximum exchange capacity of around 3.5 meq/g, a value which is too low for a very good result.

On the other hand, it is not possible to increase the content of basic groups in the resin and therefore its exchange power cannot be increased beyond said limit.

It has also been proposed (B.P. No. 1,286,949) to use ammonium or amino resins comprising a macroporous structure instead of a compact structure of the Cholestiramine type.

However these resins have never been used in practice in that the results initially obtained in vitro have not been confirmed in vivo because the methods of determination which were used experimentally were not suitable to test their capacity for stably adsorbing the cholesterol and bile acids.

In reality, the quantities of bile acids fixed in the effective times and at the effective pH values of the digestive tube for the macroporous resins are less than those obtained with the compact resins. Even the values obtained for fixing triglycerides have not been confirmed in vivo, and these resins have proved overall inferior to Cholesteramine in the plasmatic cholesterol dimension.

We have now discovered a new type of ion exchange resin specifically suitable for fixing the bile acids and forming the object of the present invention, and which by exploiting not only the chemical properties but also the physical structure attains a much higher degree of exchange power and returns the altered cholesterol levels to normal values.

The new ion exchange resin according to the present invention is characterized by the following characteristics:

a fundamental cross-linked styrene structure with active ammonium groups (strong anionic resin) or amino groups (weak anionic resin), the percentage of cross-linking being 8 to 20%.

high concentration of active groups, of 15 to 30% critical porosity in terms of the pore density of 0.3–0.6 cc/g critical porosity in terms of the pore form, specifically suitable for absorption and retention of bile salts, of an average diameter of 150 to 200 Å.

The new resin is prepared in the following stages:

1. Preparation of a cross-linked polystyrene matrix in the presence of a porosity agent.
2. Amination of the porous polystyrene matrix.

Stage 1 may be carried out in various alternative methods all of which are characterised by determined critical constant conditions, deriving from the fact that we have discovered that the quantity and in particular the form of the pores depends on:

the chemical nature and structure of the porosity agent, which must have a spacial configuration analogous to that of the steroids, must be inert under the polymerisation conditions and must be easy to eliminate without damaging the polymer when polymerisation has taken place the amount of porosity agent as a percentage by weight of the monomer mixture the polymerisation velocity the type of cross-linking agent the degree of cross-linkage. 1a. A resin matrix is prepared by copolymerising styrene with a cross-linking monomer preferably chosen from the group consisting of divinylbenzene, divinyltoluene, divinylnaphthalene, divinylxylene, divinylethylbenzene or the like.

The preferred comonomer is divinylbenzene.

The quantity of cross-linking monomer must be 8 to 20% by weight of the total weight of the monomer mixture. The polymerisation is carried out in suspension by suspending the monomer mixture in a medium in which the monomers are practically insoluble. A suitable medium is water in the presence of a dispersing agent such as the ammonium salt of a styrene-maleic anhydride copolymer, carboxymethylcellulose, bentonite or the like.

The polymerisation is of radical type and is initiated by catalysts preferably chosen from the group consisting of lauroyl peroxide, benzoyl peroxide, tertiary butyl peroxide, cumene peroxide, acetyl peroxide etc.

The quantity of catalyst required is strictly linked to the type of monomer mixture used and may vary from 0.01 to 3%, preferably 0.5 to 2% by weight of the weight of the monomers.

The quantity of porosity agent critically lies between 80 and 150% by weight.

Polymerisation is conducted in the presence of a porosity agent chosen from the group consisting of squalene, solid or liquid paraffins, hydrogenated steroids, naphthalene and similar compounds with a steroid spacial structure and a molecular weight of 200 to 500.

The best results obtained up to the present time have used squalene as the porosity agent in a 1:1 weight ratio relative to the monomer mixture.

When polymerisation has finished, the porosity agent is removed by successive extraction with a suitable, possibly hot organic solvent. Good results have been obtained with ethyl alcohol. The polymerisation velocity must be controlled within very narrow limits depending on the type and percentage of the cross-linking monomer, and the type and percentage of porosity agent.

1b. The styrene resin prepared in accordance with the process described under paragraph 1a is modified by introducing a group to which an amino compound easily adheres.

Preferably such a group is the chloromethyl group.

The chloromethylation reaction is effected using chloromethylmethylether or bis-chloromethylether.

To obtain a final ion exchange resin with a high active group content within the indicated limits of 15 and 30%, a high percentage of chloromethyl groups must be added, lying approximately within the same limits.

To obtain this result, the chloromethylation reaction must be conducted in the presence of a Lewis acid type catalyst chosen from the group consisting of:

$AlCl_3$, $ZnCl_2$, $TiCl_4$, $TiCl_3$, $SnCl_4$, $FeCl_3$.

Stage 2, namely the amination of the styrene matrix, i.e. the activation of the resin by introducing groups reactive to ion exchange, may be conducted by various alternative methods according to the type of polymer treated and the type of amino group to be introduced. However this stage may vary only chemically, as the physical structure of the resin has been fixed in the first stage of preparation and is not modified further.

2a. The porous styrene resin obtained under 1a is subjected to an amino-methylation process by reaction with diamines of the type

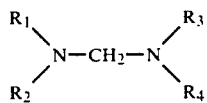

in which $R_1$, $R_2$, $R_3$, $R_4$, which may be the same or different, are alkyl groups containing 1 to 4 carbon atoms.

Under suitable conditions (temperature around 100° C. and pressure of approximately 3 atm) these diamines liberate the ion

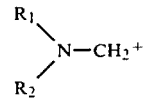

which is able to react with the free hydrogen atoms in the styrene ring.

The methyl-amino groups thus bonded to the polymer matrix may be further alkylated to attain the maximum degree of nitrogen substitution (quaternary nitrogen) with the common alkylating agents such as dimethyl sulphate and methylene chloride, bromide or iodide.

2b. The modified styrene resin obtained as described under paragraph 1b is activated by reaction with ammonia, with a dialkylamine or with a trialkylamine which are fixed to the chloromethyl groups. The products containing the free amino groups or dialkylamino groups may be further alkylated to attain the maximum degree of nitrogen substitution, with the common alkylating agents. By using this process alternative, a concentration of active groups may be attained which is greater than in the previous case and lies between 25 and 30%.

The new resin according to the invention has the following critical characteristics:
concentration of active groups: 15–30%
exchange capacity: 3.9–6 meq/g
percentage of cross-linking: 8–20%
average pore diameter: approximately 150–200 Å
specific surface area: 70–100 m²/g
porosity: 0.4–0.6 cc/g
real density: 0.9–1.1 g/cc
apparent density: 0.5–0.6 g/cc
particle size distribution: 60–80 mesh.

The aforegoing will be better clarified by some examples of preparation given hereinafter and which illustrate but do not limit the invention.

EXAMPLE 1

A mixture of 33.3 parts by weight of styrene, 16.7 parts of divinylbenzene (DVB) with a titre of 60%, and 50 parts by weight of squalene is suspended under agitation in a 20% aqueous solution of gelatine by weight. One part of bentonite is added to the suspension, and 0.2 parts by weight of lauroyl peroxide as catalyst. The suspension is heated for 40 hours at 65° C. and then for 10 hours at 90° C. The opaque pearls thus obtained are carefully washed. The squalene is then extracted with ethyl alcohol in soxelet. The extraction is followed by stripping with steam and then drying in an air current.

Part of the dry product is treated with five parts of chloromethylmethylether and two of zinc chloride at a temperature of 50° C. for seven hours to obtain a product with a 19% Cl content.

The mixture is then poured into 20 parts of $H_2O$ and neutralised with a concentrated aqueous NaOH solution.

The chloromethylated intermediate is dried, partially swollen with toluene (22% by weight) and treated with 3 parts of a 70% aqueous solution of trimethylamine at a temperature of 80° C. in an autoclave under pressure for five hours. The product is then washed firstly with water and then with a 5% NaCl solution.

A microporous anionic exchange resin is obtained with the following characteristics:
percentage of cross-linking: 11.3
exchange capacity: 3.9 meq/g
average pore diameter: approximately 200 Å
specific surface area: 70 m²/g
porosity: 0.4 cc/g
real density: 1.10 g/cc
apparent density: 0.54 g/cc
particle size distribution: 60–80 mesh.

EXAMPLE II

The polymerisation was conducted as in example I but using a monomer/porosity agent ratio of 1.2:1 and a porosity agent consisting of 70 parts of squalene, 20 parts of n-octanol and 10 parts of paraffin (41°–45° C.), to give a microporous resin of the following characteristics:
percentage of cross-linking: 11.3
exchange capacity: 4.5 meq/g
average pore diameter: approximately 190 Å
specific surface: 85 m²/g
porosity: 0.6 cc/g
real density: 1.11 g/cc
apparent density: 0.50 g/cc
particle size distribution: 60–80 mesh.

EXAMPLE III

A polystyrene matrix is prepared exactly as described in example II. However in the chloromethylation stage the catalyst used is $FeCl_3$ instead of $ZnCl_2$, but in the same ratio by weight. A chloromethylated intermediate is obtained containing 25% of Cl. This intermediate is aminated with a quantity of dimethylamine (60% solution) equal to 60% by weight of the chloromethylated product in the presence of NaOH (100%) at a temperature of 140° C. and a pressure of 10 atm for three hours.

A microporous resin is obtained of the following characteristics:
  percentage of cross-linking: 11.3
  exchange capacity: 5.7 meq/g
  average pore diameter: approximately 200 Å
  specific surface area: 85 m²/g
  porosity: 0.6 cc/g
  real density: 1.12 g/cc
  apparent density: 0.50 g/cc
  particle size distribution: 60–80 mesh.

To demonstrate the capacity of the new resins according to the invention to eliminate the bile acids present in the intestine and thus to interrupt the lipid enterohepatic cycle, some tests were carried out in vitro and in vivo and compared with a known resin (Cholestiramine) and a macroporous resin, namely Lewatit Mp-500.

The results are summarised below.

The resins used were prepared in accordance with example 2 and example 3, and identified respectively by the symbols $SSC_1$ and $SSC_2$.

1. Absorption in vitro of sodium cholate as a function of the resin quantity.

Glass containers are prepared each containing 20 ml of Na cholate at a concentration of 2 mg/ml in a 0.02 M phosphate buffer (pH6). 1 ml of $H_2O$ and increasing concentrations of the resins are added to each container.

After agitation at 25° for three minutes, the container content is filtered and the cholic acid of the filtrate is determined in total mg using the spectrophotometry method after reaction with sulphuric acid. (Kier e al., J. Clin. Invest., 40, 755, 1952). Table 1 shows the results obtained as an average of 10 tests carried out for each resin.

TABLE 1

From the values given, it is apparent that the new $SSC_1$ and $SSC_2$ resins are able to fix more sodium cholate in vitro than Cholestiramine for equal dry weights, and that the macroporous resins are much worse than Cholestiramine.

TABLE 1

| mg dry resin | 20 | 40 | 60 | 80 | 100 |
|---|---|---|---|---|---|
| Cholestiramine | 19 ± 0.8 | 12 ± 0.6 | 8 ± 0.2 | 6 ± 0.2 | 4 ± 0.8 |
| $SSC_1$ | 12 ± 0.4** | 4 ± 0.5** | ND | ND | ND |
| $SSC_2$ | 11 ± 0.3* | 8 ± 0.2* | 1 ± 0.2* | ND | ND |
| Lewatit MP 500 | 25 ± 0.8 | 23 ± 0.7 | 20 ± 0.5 | 17 ± 0.5 | 15 ± 0.5 |

ND undeterminable cholic acid
*P < 0.05 versus Cholestiramine
**P < 0.01 versus Cholestiramine 2. Absorption in vitro of sodium cholate as a function of the incubation time.

Glass containers were prepared each containing 10 ml of 0.02 M phosphate buffer of pH 6, 40 mg of sodium cholate and 20 mg of dry resin. The quantity of sodium cholate was determined at the times indicated using the spectrophotometry method of the previous paragraph 1.

TABLE 2

| | \multicolumn{4}{c}{Minutes} |
|---|---|---|---|---|
| | 3 | 5 | 10 | 20 |
| Cholestiramine | 19 ± 0.8 | 18 ± 0.8 | 6 ± 0.2 | 4 ± 0.2 |
| Lewatit MP 500 | 25 ± 0.8 | 22 ± 0.8 | 16 ± 0.5 | 10 ± 0.3 |
| $SSC_1$ | 12 ± 0.4 | 4 ± 0.5 | 2 ± 0.3 | ND |
| $SSC_2$ | 11 ± 0.3 | 5 ± 0.4 | 3 ± 0.4 | 1 ± 0.2 |

These tests clearly show that the resins according to the invention have a much greater speed of cholic acid fixing than Cholestiramine or macroporous resins.

This information is very important for the practical use of the resins in relation to the effective contact times with the bile acids in the organism.

3. Absorption in vitro of sodium cholate as a function of the pH.

The pH range considered is that effectively present in the digestive tube.

Glass containers were prepared each containing 40 mg of sodium cholate, 10 ml of 0.02 M phosphate buffer and 20 mg of dry resin. The incubation time was 10 minutes. The method for determining the cholic acid was that indicated under the previous paragraphs 1 and 2.

TABLE 3

| | pH | | | |
|---|---|---|---|---|
| | 5 | 6 | 7 | 8 |
| Cholestiramine | 5 ± 0.3 | 6 ± 0.2 | 8 ± 0.4 | 9 ± 0.5 |
| Lewatit MP 500 | 15 ± 0.5 | 16 ± 0.5 | 18 ± 0.8 | 19 ± 0.6 |
| $SSC_1$ | 2 ± 0.3 | 2 ± 0.3 | 3 ± 0.4 | 4 ± 0.4 |
| $SSC_2$ | 2 ± 0.5 | 3 ± 0.4 | 3 ± 0.4 | 4 ± 0.4 |

In this case the data obtained again indicates clearly the superiority of the new resins relative to Cholestiramine and chemically analogous macroporous resins.

4. Elimination in vivo of sodium cholate.

Male rats of Wistar stock weighing 150 g were put on a standard diet containing 1% of cholesterol and 0.5% of sodium cholate.

The rats were divided into four groups of five each.

In the first group the rats received only the standard diet. In the second group they also received Cholestiramine resin, in the third group $SSC_1$ resin and in the fourth group $SSC_2$ resin.

All the resins used were administered orally in a dose of 800 mg/kg in two administrations per day.

After seven days from the beginning of treatment, a solution of Na cholate dissolved in a phosphate buffer containing 10 mg of cholate and 0.1 uC of $C^{14}$ Na cholate was administered to the rats by gastric probe each evening for three days.

The rats were transferred into individual metabolic cages and the feces were collected for radioactivity count for three days from the beginning of the treatment with $C^{14}$ Na cholate.

The fecal radioactivity was monitored daily and the results expressed as a percentage of the controls.

With the Cholestiramine, on the first day there was an increase of 80% in the radioactivity present relative to the controls. The percentage increase was 84% and 87% on the two successive days. With $SSC_1$, the increase in radioactivity excretion on the three days was 126, 144 and 163%.

With $SSC_2$, these values were 138, 151, 149%. A statistical analysis of the data shows that these differences in the two resins relative to Cholestiramine are highly significant.

5. Elimination in vivo of cholesterol in rabbits.

Male adult rabbits of New Zealand stock were used. The rabbits were divided into five groups each containing 20 units, namely (1) controls, (2) rabbits treated with 1 g/day of cholesterol suspended in arachis oil, (3) rabbits treated with 1 g/day of cholesterol plus 0.5 g/kg/day of Cholestiramine, (4) rabbits treated with 1 g/day of cholesterol plus 0.25 g/kg/day of $SSC_1$ resins, (5) rabbits treated with 1 g/day of cholesterol plus 0.5 g/kg/day of Lewatit MP 500.

The rabbits were fed with a normal diet and treated with cholesterol using a gastric probe. A 10% suspension of gum arabic was administered to rabbits of group 3, 4 and 5 sixty minutes before the cholesterol.

After 31 days the rabbits were sacrificed and the total cholesterol was determined in the blood.

The results obtained demonstrate clearly that in vivo the macroporous resins are almost inactive, whereas the new resins according to the invention have an activity much greater than Cholestiramine.

TABLE 4

|  | Total plasmatic cholesterol, mg % |
|---|---|
| 1 - Controls | 82 ± 6 |
| 2 - 1g/day cholesterol | 713 ± 53 |
| 3 - 1g/day cholesterol + 0.50 g/kg/day Cholestiramine | ** 160 ± 12 * |
| 4 - 1g/day cholesterol + 0.25 g/kg/day $SSC_1$ | ** 108 ± 5 * |
| 5 - 1g/day cholesterol + 0.50 g/kg/day Lewatit MP 500 | 511 ± 28 * |

* $P < 0.05$ versus 2
** $P < 0.05$ versus 5

6. Elimination in vivo of cholesterol in rats.

Adult male rats of the Sprague-Dowley stock were used and were fed with a Nath diet (J. Nutrit. 67,289, 1953).

The rats were divided into five groups each containing 20 units, namely (1) controls, (2) rats fed with the Nath diet, (3) rats fed with the same diet +0.5 g/kg/day of Cholestiramine, (4) rats fed with the same diet plus 0.25 g/kg/day of $SSC_1$, (5) rats fed with the same diet plus 0.5 g/kg/day of Lewatit MP 500. After 30 days the rats were sacrificed and the total cholesterol was determined in the blood. The results, contained in the following table, show that again in this case the macroporous resins are practically inactive in vivo, and the resins according to the invention have an activity much greater than Cholestiramine.

TABLE 5

|  | Total plasmatic cholesterol, mg % |
|---|---|
| 1 - Controls | 110.4 ± 5 |
| 2 - Nath diet | 260.9 ± 13 |
| 3 - D.N. + 0.5 g/kg/day Cholestiramine | ** 120.1 ± 4 * |
| 4 - D.N. + 0.25 g/kg/day $SSC_1$ | ** 100.5 ± 7 * |
| 5 - D.N. + 0.5 g/kg/day Lewatit MP 500 | 210.2 ± 9 * |

* $P < 0.05$ versus 2
** $P < 0.05$ versus 5

Toxicity tests conducted on the resins prepared in accordance with examples 1, 2, 3 indicate that the $LD_{50}$ was not determinable. Clinically conducted tests confirmed the results obtained in the laboratory tests, and in fact the superiority of the new resins relative to Cholestiramine was more marked.

Therapeutic doses lie between 8 and 20 g/day with an administration of 2-7 g one hour before meals.

What is claimed is:

1. In a method for preparing a microporous anionic resin which comprises treating styrene with a cross-linking monomer in the presence of a porosity agent and with a catalyst initiator to afford copolymerized styrene resin, followed by the introduction into said resin of amino, alkylamino, dialkylamino or quaternary ammonium moieties; the improvement which comprises using as the porosity agent squalene or an hydrogenated steroid having a molecular weight of from about 200–500 in a proportion of from about 80–150% by weight of the total weight of the monomer mixture.

2. The method according to claim 1 which comprises:
   (1) treating styrene with 8–20% by weight of a cross-linking monomer selected from divinylbenzene, divinyltoluene, divinylnaphtalene, divinylxylene or divinylethylbenzene, in the presence of 80–150% by weight of squalene and with 0.5–2% by weight of a catalyst initiator to afford copolymerized sytrene resin, all weights being based on the total weight of the monomer mixture;
   (2) treating the resin of step (1) with chloromethylmethyl ether or bis-chloromethyl ether, in the presence of a lewis Acid catalyst, to afford a chloromethyl substituted styrene resin; and
   (3) subjecting the resin of step (2) to treatment with ammonia, alkylamine, dialkylamine or a trialkylamine to afford a microporous resin having a cross-linked polystyrene matrix comprised of active moieties selected from amino, alkylamino, dialkylamino or trialkylammonium.

3. The method of claim 2 wherein squalene is employed as the porosity agent in a 1:1 weight ratio with respect to the monomer mixture.

4. A method according to claim 2 for the preparation of a microporous anionic resin characterized by the following properties:
   percentage of cross-linking: 11.3
   exchange capacity: 3.9 meq/g
   average pore diameter: 200 Å
   specific surface area: 70 m²/g
   porosity: 0.4 cc/g
   real density: 1.10 g/cc
   apparent density: 0.54 g/cc
   particle size distribution: 60–80 mesh
which comprises:
   (1) treating styrene with divinylbenzene in the presence of squalene in an aqueous solution of gelatin; adding lauroyl peroxide as a catalyst and extracting residual squalene with ethyl alcohol to afford a copolymerized resin;

(2) treating the resin of step (1) with chloromethylmethyl ether and zinc chloride to afford the corresponding chloromethyl intermediate; and (3) subjecting the intermediate of step (2) to treatment with trimethylamine to afford the desired product.

5. A microporous anionic resin prepared according to the process of claim 1 having a cross-linked polystyrene matrix comprised of active moieties selected from amino, alkylamino, dialkylamino or trialkylammonium, characterized by the following properties:
percentage of cross linking: 8–20%
exchange capacity: 3.9–6 meq/g
porosity: 0.4–0.6 cc/g
average pore diameter: 150–200 Å
specific surface area: 70–100 $m^2$/g
real density: 0.9–1.1 g/cc
apparent density: 0.5–0.6 g/cc
particle size distribution: 60–80 mesh.

6. The resin according to claim 5 wherein the active moieties are selected from methylamino, trimethylammonium or a combination of methylamino and trimethylammonium.

7. The resin according to claim 5 wherein the active moieties are trimethylammonium and said product is characterized by the following properties:
percentage of cross linking: 11.3%
exchange capacity: 3.9 meq/g
porosity: 0.4 cc/g
average pore diameter: 200 Å
specific surface area: 70 $m^2$/g
real density: 1.10 g/cc
apparent density: 0.54 g/cc
particle size distribution: 60–80 mesh.

8. The resin of claim 5 wherein the active moieties are dimethylamino and said product is characterized by the following properties:
percentage of cross linking: 11.3
exchange capacity: 5.7 meq/g
average pore diameter: 200 Å
specific surface area: 85 $m^2$/g
porosity: 0.6 cc/g
real density: 1.12 g/cc
apparent density: 0.50 g/cc
particle size distribution: 60–80 mesh.

9. A therapeutic composition having hypocholesterolemic activity which comprises as the active ingredient an anionic microporous resin prepared according to the process of claim 1 having a cross-linked polystyrene matrix comprised of active moieties selected from among methylamino, trimethylammonium or a combination of methylamino and trimethylammonium, characterized by the following properties:
percentage of cross linking: 8–20%
exchange capacity: 3.9–6 meq/g
porosity: 0.4–0.6 cc/g
average pore diameter: 150–200 Å
specific surface area: 70–$100^2$ m/g
real density: 0.9–1.1 g/cc
apparent density: 0.5–0.6 g/cc
particle size distribution: 60–80 mesh
in combination with an inert pharmacologically acceptable carrier.

10. The method of treating hypercholesterolemia which comprises administering to a host an effective amount of a resin prepared according to the process of claim 1 having a cross-linked polystyrene matrix comprising active moieties selected from among methylamino, trimethylammonium or a combination of methylamino and trimethylammonium, characterized by the following properties:
percentage of cross linking: 8–20%
exchange capacity: 3.9–6 meq/g
porosity: 0.4–0.6 cc/g
average pore diameter: 150–200 Å
specific surface area: 70–100 $m^2$/g
real density: 0.9–1.1 g/cc
apparent density: 0.5–0.6 g/cc
particle size distribution: 60–80 mesh.

* * * * *